US010278746B2

(12) United States Patent
Deneuvillers et al.

(10) Patent No.: US 10,278,746 B2
(45) Date of Patent: May 7, 2019

(54) ACCESSORY FOR TENSIONING AN ELONGATE ELEMENT

(71) Applicant: COUSIN BIOTECH, Wervicq Sud (FR)

(72) Inventors: Guy Deneuvillers, Merlimont (FR); Jules Prandi, Tourcoing (FR)

(73) Assignee: COUSIN BIOTECH, Wervicq Sud (FR)

(*) Notice: Subject to any disclaimer, the term of this patent is extended or adjusted under 35 U.S.C. 154(b) by 0 days.

(21) Appl. No.: 15/516,033

(22) PCT Filed: Sep. 30, 2015

(86) PCT No.: PCT/FR2015/052617
§ 371 (c)(1),
(2) Date: Mar. 31, 2017

(87) PCT Pub. No.: WO2016/051088
PCT Pub. Date: Apr. 7, 2016

(65) Prior Publication Data
US 2017/0354445 A1 Dec. 14, 2017

(30) Foreign Application Priority Data
Oct. 1, 2014 (FR) .................................. 14 596366

(51) Int. Cl.
A61B 17/88 (2006.01)
A61B 17/70 (2006.01)
(Continued)

(52) U.S. Cl.
CPC ...... *A61B 17/7083* (2013.01); *A61B 17/8861* (2013.01); *A61B 17/8869* (2013.01);
(Continued)

(58) Field of Classification Search
CPC ............ A61B 17/7083; A61B 17/8869; A61B 17/8861; A61B 17/842; A61B 17/82; A61B 17/88
See application file for complete search history.

(56) References Cited

U.S. PATENT DOCUMENTS 1,347,579 A * 7/1920 Henrikson ............ B25B 25/005
606/103
1,950,799 A * 3/1934 Jones ...................... A61B 17/82
606/286
(Continued)

FOREIGN PATENT DOCUMENTS

EP 1878397 A1 1/2008
EP 1933743 B1 3/2011
(Continued)

OTHER PUBLICATIONS

International Search Report and Written Opinion dated Jan. 7, 2016, International Application No. PCT/FR2015/052617, pp. 1-15 (including English Translation).

*Primary Examiner* — Eduardo C Robert
*Assistant Examiner* — Michelle C Eckman
(74) *Attorney, Agent, or Firm* — MH2 Technology Law Group, LLP

(57) ABSTRACT

The present invention provides a tensioning ancillary instrument (5) for tensioning an elongate element to fasten an implant on a portion of bone, by surrounding said portion of bone at least in part, said instrument (5) comprising a body (6) having proximal and distal ends (6a, 6b), the distal end (6a) being provided with a device for bearing against the implant, said body (6) extending along a longitudinal axis (L). The instrument (5) further comprising a carriage (7) that is movable along the longitudinal axis (L), and a fastener device (8) for fastening to the elongate element (2). The instrument (5) also includes a rotary shaft (9) rotatable about (Continued)

the longitudinal axis (L) of the body (6), the shaft (9) being configured to co-operate with the carriage (7) in such a manner that rotation of the shaft (9) drives movement of the carriage (7) in translation along the longitudinal axis (L) and correspondingly moves the carriage (7) away from the distal end (6b) of the body (6) and tensions the elongate element.

21 Claims, 6 Drawing Sheets

(51) Int. Cl.
    *A61B 90/00*           (2016.01)
    *A61B 17/00*           (2006.01)
    *A61B 17/90*           (2006.01)

(52) U.S. Cl.
    CPC ............ *A61B 2017/00367* (2013.01); *A61B 2017/00477* (2013.01); *A61B 2017/00862* (2013.01); *A61B 2017/90* (2013.01); *A61B 2090/034* (2016.02)

(56) References Cited

U.S. PATENT DOCUMENTS

| | | | | |
|---|---|---|---|---|
| 2,049,361 | A * | 7/1936 | Ericsson | A61B 17/8861 100/32 |
| 2,279,068 | A * | 4/1942 | Siebrandt | A61B 17/8861 140/121 |
| 2,291,413 | A * | 7/1942 | Siebrandt | A61B 17/8861 140/121 |
| 2,414,746 | A * | 1/1947 | Karle | A61B 17/04 112/254 |
| 2,455,609 | A * | 12/1948 | Scheib | A61B 17/8861 140/121 |
| 2,943,650 | A * | 7/1960 | Rubin | A61B 17/8861 140/119 |
| 3,507,270 | A * | 4/1970 | Ferrier | A61B 5/02233 24/135 R |
| 3,759,302 | A * | 9/1973 | Attenborough | B21F 15/04 140/119 |
| 4,732,180 | A * | 3/1988 | Fixel | B65B 13/28 140/119 |
| 4,966,600 | A * | 10/1990 | Songer | A61B 17/8861 606/103 |
| 5,116,340 | A * | 5/1992 | Songer | A61B 17/8861 29/282 |
| 5,312,410 | A * | 5/1994 | Miller | A61B 17/8861 606/103 |
| 5,395,374 | A * | 3/1995 | Miller | A61B 17/82 606/103 |
| 5,536,270 | A * | 7/1996 | Songer | A61B 17/823 606/103 |
| 5,788,697 | A * | 8/1998 | Kilpela | A61B 17/8869 254/199 |
| 5,830,234 | A * | 11/1998 | Wojciechowicz | A61B 17/06166 606/224 |
| 6,752,810 | B1 * | 6/2004 | Gao | A61B 17/8861 606/103 |
| 7,094,240 | B2 * | 8/2006 | Molz, IV | A61B 17/88 606/103 |
| 8,029,513 | B2 * | 10/2011 | Konno | A61B 17/8861 606/103 |
| 8,162,946 | B2 | 4/2012 | Baccelli et al. | |
| 8,814,910 | B2 | 8/2014 | Baccelli et al. | |
| 8,932,296 | B2 * | 1/2015 | Neary | A61B 17/7077 606/86 A |
| 9,179,942 | B2 | 11/2015 | Guizzardi et al. | |
| 9,393,051 | B2 | 7/2016 | Baccelli et al. | |
| 9,603,646 | B2 * | 3/2017 | Voisard | A61B 17/8861 |
| 9,820,793 | B1 * | 11/2017 | Wade | A61B 17/8869 |
| 2003/0178611 | A1 * | 9/2003 | Anderson | B63B 15/02 254/231 |
| 2003/0208210 | A1 * | 11/2003 | Dreyfuss | A61B 17/0469 606/144 |
| 2005/0177179 | A1 * | 8/2005 | Baynham | A61B 17/82 606/151 |
| 2006/0167464 | A1 * | 7/2006 | Allen | A61B 17/8869 606/103 |
| 2008/0262551 | A1 * | 10/2008 | Rice | A61B 17/7085 606/268 |
| 2009/0082776 | A1 * | 3/2009 | Cresina | A61B 17/8861 606/103 |
| 2009/0105715 | A1 * | 4/2009 | Belliard | A61B 17/7053 606/103 |
| 2009/0138048 | A1 | 5/2009 | Baccelli et al. | |
| 2010/0030240 | A1 * | 2/2010 | Brailovski | A61B 17/823 606/144 |
| 2010/0042106 | A1 * | 2/2010 | Bryant | A61B 17/8869 606/103 |
| 2010/0057091 | A1 * | 3/2010 | Oosterom | A61B 17/8861 606/103 |
| 2010/0087836 | A1 * | 4/2010 | Jaramillo | A61B 17/04 606/144 |
| 2010/0087837 | A1 * | 4/2010 | Jaramillo | A61B 17/04 606/144 |
| 2011/0106185 | A1 * | 5/2011 | Gil | A61B 17/7022 606/86 R |
| 2011/0112537 | A1 * | 5/2011 | Bernstein | A61B 17/8869 606/74 |
| 2012/0123447 | A1 * | 5/2012 | Corrao | A61B 17/04 606/144 |
| 2012/0197256 | A1 * | 8/2012 | Knueppel | A61B 17/823 606/74 |
| 2012/0265260 | A1 * | 10/2012 | Yamaguchi | A61B 17/8869 606/86 R |
| 2013/0072983 | A1 * | 3/2013 | Lindquist | A61B 17/7049 606/278 |
| 2013/0167334 | A1 * | 7/2013 | Gephart | A61B 17/8861 24/69 R |
| 2013/0184720 | A1 * | 7/2013 | Aldridge | A61B 17/8861 606/148 |
| 2013/0261625 | A1 * | 10/2013 | Koch | A61B 17/1604 606/74 |
| 2014/0100582 | A1 * | 4/2014 | Koch | A61B 17/8071 606/101 |
| 2014/0142638 | A1 * | 5/2014 | Goodwin | A61B 17/842 606/281 |
| 2014/0257397 | A1 * | 9/2014 | Akbarnia | A61B 17/7053 606/263 |
| 2014/0257401 | A1 * | 9/2014 | George | A61B 17/7041 606/278 |
| 2014/0276896 | A1 * | 9/2014 | Harper | A61B 17/7086 606/104 |
| 2014/0277207 | A1 * | 9/2014 | Baccelli | A61B 17/7053 606/86 A |
| 2014/0303625 | A1 * | 10/2014 | Sholev | A61B 17/0482 606/80 |
| 2015/0342657 | A1 * | 12/2015 | Voisard | A61B 17/823 606/103 |
| 2016/0249957 | A1 | 9/2016 | Deneuvillers | |
| 2016/0262806 | A1 * | 9/2016 | Hsu | A61B 17/7076 |
| 2016/0317161 | A1 * | 11/2016 | Garcia | A61B 17/1611 |
| 2016/0331431 | A1 * | 11/2016 | Gephart | A61B 17/8076 |
| 2017/0172633 | A1 * | 6/2017 | Simpson | A61B 17/8869 |
| 2017/0265906 | A1 * | 9/2017 | Akbarnia | A61B 17/8869 |
| 2017/0354445 | A1 * | 12/2017 | Deneuvillers | A61B 17/7083 |
| 2018/0014825 | A1 * | 1/2018 | Sholev | A61B 17/0642 |
| 2018/0021077 | A1 * | 1/2018 | Simpson | A61B 17/7076 |

FOREIGN PATENT DOCUMENTS

| | | |
|---|---|---|
| EP | 2609882 A1 | 12/2012 |
| EP | 2609882 A1 | 7/2013 |
| EP | 2555698 B1 | 4/2014 |

(56) References Cited

FOREIGN PATENT DOCUMENTS

| | | |
|---|---|---|
| FR | 2890851 A1 | 3/2007 |
| FR | 2981841 A1 | 5/2013 |
| WO | 2015/007985 A1 | 1/2015 |

* cited by examiner

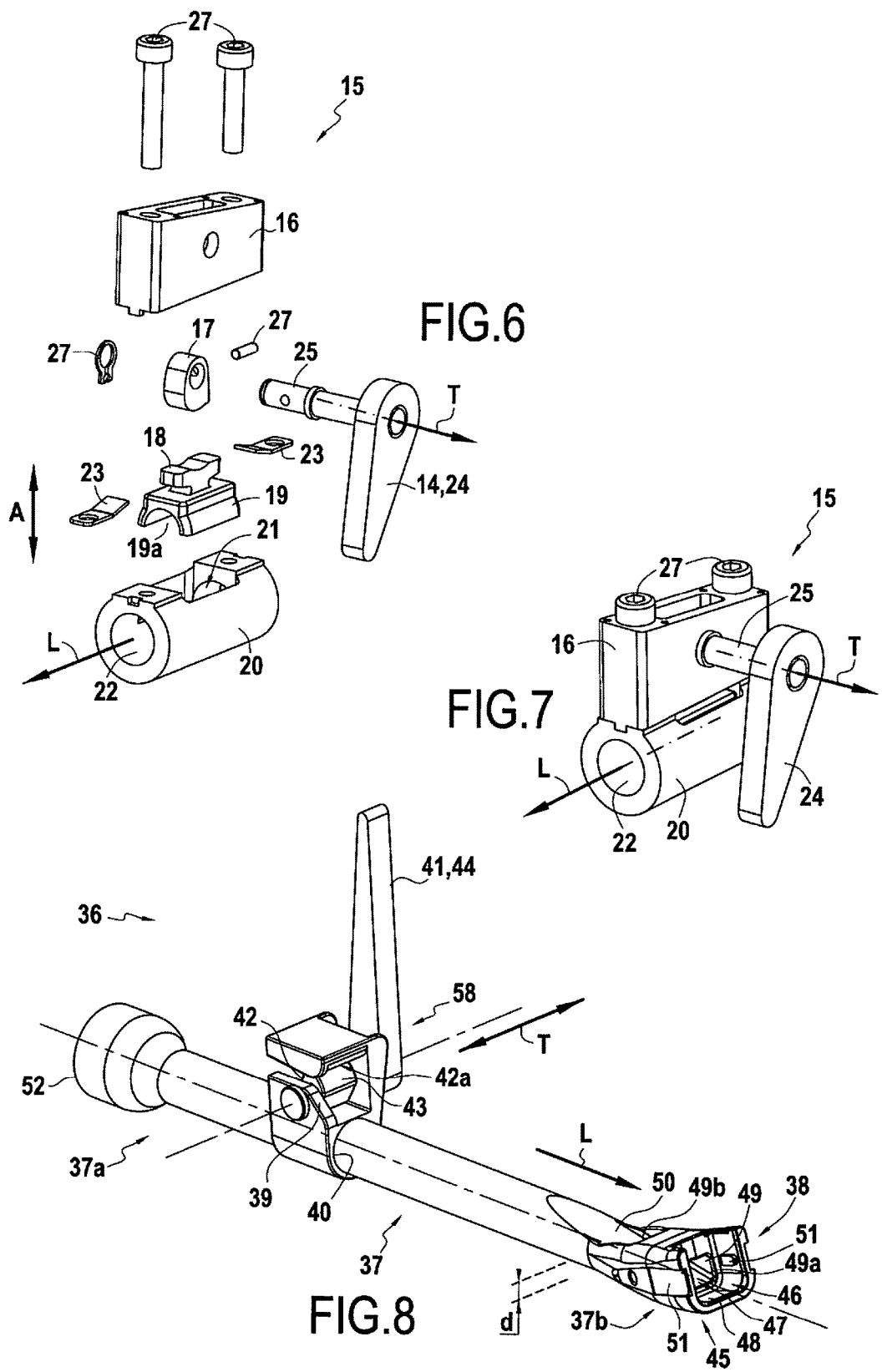

ACCESSORY FOR TENSIONING AN ELONGATE ELEMENT

The present disclosure relates to the technical field of ancillary instruments for tensioning an elongate element, in particular a flat element, in order to fasten an implant on a portion of bone, and in particular on at least a portion of a vertebral body.

BACKGROUND OF THE DISCLOSURE

It is known to correct abnormal curvature of the spine and/or pathological inclinations between vertebrae by using longitudinal bars that are arranged on either side of the vertebral column and that are secured to the vertebrae by screws inserted in the vertebrae themselves or by hooks, e.g. inserted along the spinal canal.

Nevertheless, such screws and hooks have the disadvantages of being aggressive for the spine.

In order to mitigate those drawbacks, proposals have been made for a flexible elongate fastener element combined with an implant suitable for being secured to a longitudinal bar, the elongate element being fastened to the implant and engaging at least a portion of a vertebra by forming a loop about that portion.

The longitudinal bars can be used for treating sclerosis or indeed for treating degenerative pathologies. Various different levels of degeneration are encountered, e.g. involving one vertebra, such as discopathy, or two vertebrae, such as spondylolisthesis, or indeed several vertebral levels such as C- or S-sclerosis.

In such treatments, the longitudinal bar needs to be connected with the vertebral level for correction by using an elongate element, which passes around at least a portion of a vertebral body and around said bar with the ends of said elongate element possibly being held by means of a suture or a knot, or by using implantable connection means. By way of example, said connection means may comprise a housing receiving the longitudinal bar and the elongate element wound around the bar, together with clamping means for blocking the bar and said elongate element in said housing. In general, the clamping means comprise means that pinch said elongate element so as to prevent any movement thereof.

One of the problems that the present disclosure seeks to solve is putting the elongate element under tension when it forms a loop over at least a portion of a vertebral body, and is engaged with an implant and/or a longitudinal bar.

EP 1 933 743 B1 relates to a tensioning instrument for tensioning an elongate element comprising a movable cylindrical part suitable for moving in translation around a rod, said rod having bearing means at its distal end for bearing against a longitudinal bar and not against the implant that receives the bar the elongate element. The movable cylindrical part also includes a lug for fastening the elongate element. The torque clamping system can be actuated by means of a handle. The elongate element is tensioned by the surgeon pressing on the handle without limit on the tension that can be applied. No portion of the instrument is adapted to allow the elongate element to move, the element merely being tensioned between two points (i.e. the implant and the lug) and being put under tension without there being any movement of the elongate element in a portion of the instrument. With that clamping system, the surgeon can apply excessive tension on the elongate element, running the risk of spoiling the adjustment of the longitudinal bar(s) placed on the vertebral level(s) for correction, or indeed the risk of moving the vertebrae. In addition, the tension is applied on a loop in line with two free ends of the elongate element that are held together with a keeper. The tension that is applied is therefore not the same on both of the free ends since it is applied directly to only one free end of the elongate element that extends the other free end via the loop. Tension is thus applied in unbalanced manner on the free ends of the elongate element and runs the risk of eroding the vertebral portion on which the tension is applied and/or the risk of the elongate element sliding on said vertebral portion.

In contrast with EP 1 933 743 B1, FR 2 981 841 A1 provides a tensioning ancillary instrument seeking to avoid the elongate element becoming twisted while it is being tensioned. The instrument thus includes a deflector so that the elongate element forms a 90° angle. The ends of the elongate element provided with securing means are fastened to a compensation wheel at two diametrically opposite points. The tension applied to each of the ends of the elongate element is thus not balanced. Furthermore, the deflector for deflecting the elongate element through 90° and the means for fastening one end in a cut gives rise to high level of friction on the elongate element, running the risk of weakening it. Furthermore, because of the deflector member, the instrument is bulky. Unfortunately, during surgery, many implants and longitudinal bars may be put into place on the vertebral level(s) for correction so that, once the elongate element has been put under tension, it is important for the surgeon to be able to have easy access to the implant in order to finish off tightening and fastening the implant on the elongate element, and also in order to have access to the other implants and/or longitudinal bars.

SUMMARY OF THE DISCLOSURE

An object of the present disclosure is thus to provide a tensioning ancillary instrument suitable for tensioning an elongate element forming a loop over at least a portion of a vertebral body without damaging said vertebral body, and that is progressive and easily adjustable by the surgeon.

The present disclosure also seeks to provide a tensioning ancillary instrument suitable for exerting equal tension on each of the two ends of the elongate element.

Another object of the present disclosure is to provide a tensioning ancillary instrument enabling the surgeon to release rapidly the tension exerted on the elongate element, should that be necessary, and to apply controlled tension on the elongate element, in particular tension that does not exceed a determined value.

In a first aspect, the present disclosure provides a tensioning ancillary instrument for tensioning an elongate element, in particular a flat element, to fasten an implant on a portion of bone, in particular at least a portion of a vertebral body, by surrounding said portion of bone at least in part, said instrument comprising a body having proximal and distal ends, the distal end being provided with a device for bearing against the implant, said body extending along a longitudinal axis, the instrument further comprising a carriage that is movable along the longitudinal axis, and a fastener device for fastening to the elongate element. In characteristic manner, the instrument includes a rotary shaft rotatable about the longitudinal axis of the body, the shaft being configured to co-operate with the carriage in such a manner that rotation of the shaft drives movement of the carriage in translation along the longitudinal axis and correspondingly moves the carriage away from the distal end of the body and tensions the elongate element.

The instrument of the disclosure may also include a clutching and declutching device for clutching and declutching the carriage and the rotary shaft, the carriage having a declutched position in which the carriage is free to slide longitudinally relative to the longitudinal axis (l) of the rotary shaft, and a clutched position in which the carriage is coupled with the rotary shaft.

The elongate element may be tensioned along the longitudinal axis of the body receiving the movable carriage, thereby reducing the overall size of the instrument in operation and facilitating tensioning.

In particular, the elongate element is put under tension along a path parallel to the longitudinal axis extending between the bearing device and the fastener device.

The carriage may include the fastener device for fastening the elongate element.

Furthermore, with the carriage mounted on a rotary shaft, the instrument of the disclosure has no need for a system for preventing reversal of the elongate element. Specifically, when the tension applied on the elongate element is released, the carriage no longer moves and remains stationary since it is held by the rotary shaft.

The elongate element of the disclosure may be a textile element, that may be braided, knitted, or woven, and that may be braided. The elongate element may be flat so as to generate large friction forces on the surfaces against which it moves, thereby improving the clamping forces.

The elongate element has first and second ends, which may possibly be free.

The bearing device comes to bear against the implant, which may include a connector and/or implantable means for securing the elongate element to a longitudinal bar and/or an ancillary instrument for pre-tensioning the elongate element, such as the instrument described below with reference to the second aspect of the disclosure.

The bearing device of the tensioning instrument may be the bearing device of the pre-tensioning instrument that is described below, independently of the other characteristics of the pre-tensioning instrument.

The connector may be the connector described in international patent application PCT/FR2014/051801 filed in the name of the Applicant, the description of which is incorporated in the present text.

The implantable securing means may be the means described in patents EP 2 555 698 B1 and EP 2 609 882 A1.

The carriage may be configured to receive at least two superposed portions of the elongate element, thereby improving the distribution of tension in the elongate element and avoiding risks of erosion and/or slipping of the elongate element around the portion of the vertebral body.

The rotary shaft may be a threaded shaft, and may have a helical thread.

In the present text, the term "suitable for" is equivalent to the following terms, considered independently of one another: "for", "configured to", "suitable for allowing", "suitable for complying with".

In a variant, the shaft includes a portion extending beyond the proximal end of the body and configured to be coupled with a torque actuator device.

It may be possible to select accurately the torque (newton-centimeters) that it is desired to apply for tensioning the elongate element instead of exerting an approximate tension for which the torque is not known, with this being safer for the patient.

In a variant, the fastener device may comprise a jaw-forming assembly extending in two planes (p1, p2) that slope relative to each other and that slope relative to the longitudinal axis of the body.

The jaw-forming assembly may include a left side jaw and a right side jaw that move apart from each other to receive at least a portion of the elongate element, each lying in a respective sloping plane (p1, p2).

In another variant, the fastener device includes a jaw-forming assembly having a top jaw and a bottom jaw, the top jaw extending in a plane (p3) that slopes relative to the bottom jaw and/or relative to the longitudinal axis of the cylindrical body. The bottom jaw may be in a plane (i) parallel to the longitudinal plane (P) of the cylindrical body. The top jaw may move away from the bottom jaw (which is itself stationary relative to the top jaw, since it is secured to the clutching and declutching device), in order to receive at least a portion of the elongate element in a plane (T1) that extends transversely, possibly substantially perpendicularly, relative to the longitudinal plane (P) of the cylindrical body.

The elongate element (at least two superposed portions thereof) may be pinched between said top and bottom jaws so as to be arranged in a plane that is parallel to the longitudinal plane (P) of the cylindrical body.

In either of the above two variants, each of the left and right side jaws or the top and bottom jaws may have a respective face with a contact portion that comes into contact with a portion of the elongate element. Said contact portions are knurled, and in particular they include pyramid-shaped knurling. The pyramid-shaped knurling of a given contact portion may be arranged in a staggered configuration relative to the knurling of the opposite contact portion (placed facing the given contact portion) so as to improve the pinching and thus the blocking of the elongate element.

In the two above variants, this jaw-forming assembly constitutes a fastener device for fastening the elongate element to the carriage.

The surgeon has no need to have special means on the free ends of the elongate element in order to cause them to co-operate with a fastener system on the instrument or to form a loop, as is necessary in the prior art. It thus suffices merely to superpose the first and/or second free end(s) of the elongate element in the jaw-forming assembly after moving the jaws apart from each other by using the grip member as described below.

The slope of the jaw-forming assembly or of the top jaw may enable tension to be applied progressively on the elongate element, thereby improving the force fastening the elongate element to the fastener device. The two planes of the left and right lateral jaws may converge towards the distal end of the body, thereby further improving the above-mentioned effects.

The jaw-forming assembly or the top jaw also slopes relative to the longitudinal axis of the cylindrical body so that the elongate element adopts a corresponding slope between said assembly and the distal end of the body.

This provision also avoids the elongate element deactivating the anti-reverse blocker of the pre-tensioning instrument of the disclosure, as described below.

In a variant, the jaws (in particular the left and right lateral jaws) or the top jaw is/are configured to be movable and actuatable by a grip member in order to place the elongate element between said jaws.

The jaw-forming assembly may include a locking member serving to block said jaws in an open position. The locking member may have facing lugs arranged in said grip member, in particular a tie, the lugs being suitable for coming into abutment against the carriage in order to block the jaw-forming assembly in the open position.

In a variant, the instrument includes a rapid unlocking device for decoupling the carriage from the rotary shaft.

This provision makes it possible to release the tension on the elongate element automatically, thereby providing safety for the surgeon while adjusting the elongate element.

In a variant, the clutching and declutching device includes a rapid unlocking device for actuating the declutching and clutching of the carriage with the rotary shaft.

In a variant, the clutching and declutching device includes a cam mounted on a return member associated with the rapid unlocking device enabling the carriage to be passed from the clutched position to the declutched position, and vice versa.

In a subvariant, the clutching and declutching device includes a housing suitable for receiving the rotary shaft, said housing having a window suitable for passing a fork associated with the carriage in order to clutch or declutch the rotary shaft under the effect of the cam mounted on said return member.

In a variant, the body includes a spring, in particular a cylindrical spring, mounted on the rotary shaft and extending longitudinally between a proximal end of the body and the carriage.

The spring bears against the proximal end of the body and against the carriage, thereby accelerating the release of tension on the elongate element when the rapid unlocking device is actuated to decouple the carriage from the rotary shaft, since the spring pushes the carriage towards the distal end of the body.

In a variant, the carriage includes a longitudinal slot for receiving the elongate element, in particular two superposed portions of said elongate element.

The tension may be applied uniformly on the elongate element forming a loop around the portion of the vertebral body and the longitudinal bar.

In a subvariant, the slot is arranged above the jaw-forming assembly.

This provision facilitates access to the jaw-forming assembly and thus facilitates arranging the elongate element in said assembly.

In a variant, the rapid unlocking device includes a lever that is configured, when actuated, to decouple the carriage from the rotary shaft.

In a variant, the proximal end of the body includes a coupling member suitable for being coupled with a removable handle and configured so as to allow the handle to pivot about the longitudinal axis of the body.

The coupling member may also be configured to block the handle in a determined position about the longitudinal axis of the body.

The surgeon can thus modify the position of the handle by pivoting the handle around the body about the longitudinal axis of the body. The removable handle may include a ring having at least one tooth on its periphery suitable for co-operating with a notch in a notched ring mounted on the proximal end of the body. The coupling member may have a clamping ring that clamps together the notched ring and the ring including at least one tooth in order to block the coupling between said rings. In particular, the proximal end of the body includes a threaded portion on which the clamping ring can be screwed.

In a second aspect, the present disclosure provides an assembly comprising a tensioning instrument according to any of the above embodiment variants, and a pre-tensioning ancillary instrument including a bearing device, where said device for bearing against the implant is the bearing device of said pre-tensioning instrument.

In a variant, the instrument for pre-tensioning the elongate element, in particular a flat element, for fastening the implant on a portion of bone, in particular at least a portion of a vertebral body, by surrounding said portion of bone at least in part, includes a rod having proximal and distal ends, the distal end being provided with a bearing device for bearing against said implant, said rod extending along a longitudinal axis. The rod may include a guide and blocking device for guiding and blocking the elongate element along the longitudinal axis, and said guide and blocking device includes an anti-reverse blocker allowing the elongate element to move in said guide and blocking device longitudinally towards the proximal end of the rod, and preventing the elongate element moving longitudinally towards the distal end of the rod.

The anti-reverse blocker may prevent any movement of the elongate element towards the distal end of the rod when no tension is exerted on the elongate element, thereby facilitating the work of the surgeon and enabling the surgeon to leave the elongate element waiting while performing other acts. The surgeon can then return to tensioning the elongate element without needing to exert any other prior action on the pre-tensioning instrument.

The elongate element may be tensioned along a path parallel to the longitudinal axis of the rod between the distal end of the rod and the anti-reverse blocker.

The elongate element may be tensioned along a path parallel to the longitudinal axis of the rod of the pre-tensioning instrument and to the longitudinal axis of the body of the tensioning instrument, the longitudinal axes of the bodies and of the rod being parallel.

The anti-reverse blocker may be configured to receive at least two superposed elongate element portions, said portions respectively extending first and second free ends of the elongate element.

The bearing device comes to bear against the implant that may include a connector and/or implantable securing means for securing the elongate element to an elongate bar, and/or an elongate bar.

In a variant, the anti-reverse blocker includes an unlocking member that, when actuated, allows the elongate element to move longitudinally towards the distal end of the rod.

The unlocking member may enable the tension exerted on the elongate element to be released automatically, thereby providing safety for the surgeon.

The anti-reverse blocker may include a cam mounted on a return spring and engaging at least one portion of the elongate element, for example at least two superposed portions of the elongate element, against a bearing surface, in particular a top bearing surface, in order to block movement of the elongate element towards the distal end of the rod.

The unlocking member may be a lever that acts on the cam and disengages it from the elongate element.

In a variant, the anti-reverse blocker has a longitudinal passage with a top bearing surface constituting a guide portion for guiding the longitudinal movement of the elongate element.

When the elongate element is flat, friction against the bearing surface may be amplified and may improve the guidance and blocking of the elongate element against said top bearing surface.

In a variant, the guiding and blocking device further comprises a blocking element configured to block the elongate element against the top bearing surface, while preventing the elongate element from moving longitudinally towards the distal end of the rod.

The blocking element may include a return member for returning it to its initial position corresponding to its engagement, and thus to blocking the elongate element against said bearing surface. When the elongate element is tensioned, thereby causing it to move towards the proximal end of the rod, the blocking element, under the effect of the elongate element, disengages therefrom and thus from the top bearing surface.

The top bearing surface may slope relative to the longitudinal axis of the rod in order to avoid the blocking element, in particular a cam mounted on a return spring, remaining in contact with the elongate element and disengaging from said elongate element under the effect of the elongate element itself, depending on the angle at which tension is applied thereto.

For example, the spring may be cylindrical or flat.

In particular, the return member is mounted between the unlocking member having an actuator lever and the blocking element, for example around a rod connecting said lever to said blocking element.

In particular, the blocking element blocks the elongate element against the bearing surface, and thus when the elongate element has at least two superposed portions (in particular extending each of its first and second free ends), a first portion is arranged between the top bearing surface and the second portion, while the second portion is arranged between the first portion and the blocking element.

In a variant, the blocking element is mounted rotatably about an axis extending transversely to the longitudinal direction of the rod.

The blocking element may have a curved contact portion contacting the elongate element in order to avoid damaging the elongate element by abrasion.

In a variant, the guiding and blocking device is configured to have two superposed portions of the elongate element passed therethrough.

Each of the portions may extend one of the two free ends of the elongate element so that the tension exerted on the elongate element is applied uniformly to the entire loop surrounding at least part of said vertebral body, thereby avoiding any risk of said elongate element slipping, and thus any risk of eroding said vertebral body.

The guiding and blocking device may include a lateral opening facilitating insertion of said superposed portions of the elongate element.

In a variant, the unlocking member includes a lever configured to actuate the blocking element.

The lever may be in connection with the blocking element and is suitable for causing said blocking element to pivot towards the proximal end of the rod in order to allow the elongate element (the two superposed portions) to move towards said distal end of the rod.

In a variant, the distal end of the rod may have a head that includes the bearing device, the head is provided with a housing configured to receive at least a portion of the implant, the housing having an opening for passing and guiding the elongate element.

The housing may be configured to receive a connector or implantable means for securing the elongate element to a longitudinal bar.

The opening may be a duct leading to a window or a groove.

In a variant, the opening may have a bottom wall that slopes relative to the longitudinal axis of the rod for guiding the elongate element towards the guiding and blocking device.

During surgery, the implant, and in particular the connector or the implantable securing means, may be thus disengaged and enables the surgeon to have easy access to the implant e.g. with a screwdriver, in order to finish off fastening the elongate element without being hindered by spinus processes while accessing the implantation zone.

In a variant, the head may slope relative to the longitudinal axis of the rod and forms a bearing zone bearing on the implant that slopes relative to a plane passing perpendicularly to the longitudinal axis.

The above-described technical effect is thus provided.

In a variant, the opening may form a duct leading to a window, said duct having an inlet orifice and an outlet orifice for the elongate element that are spaced apart by a determined distance.

When the elongate element leaves the connector or the implantable securing means, it may be guided by the window in order to be tensioned not directly on leaving the implant, but at the outlet from the window so as to avoid impeding use of the fastener member of the implant for fastening the elongate element to said implant.

In a variant, the duct may include top and bottom walls, the bottom wall being the sloping bottom wall.

In a variant, the opening may include a coupling member, in particular a removable member, for coupling with the implant in order to secure the head in releasable manner with the implant.

The coupling member may have flyweights mounted on a return member, e.g. a flat spring, suitable for co-operating with a corresponding coupling member on the implant, e.g. through lateral openings.

In a variant, the proximal end of the rod may be provided with a coupling member for coupling with a tensioning instrument.

The proximal end may receive a handle.

The present disclosure can be better understood on reading the description below of embodiments given in non-limiting manner and shown in the drawings accompanying the present text.

DETAILED DESCRIPTION OF THE DRAWINGS

FIG. 6 is an exploded view of the device for clutching and declutching the carriage on the rotary shaft of the instrument shown in FIGS. 2 to 5;

FIG. 7 is a diagrammatic perspective view of the device for clutching and declutching the carriage on the rotary shaft of the instrument shown in FIGS. 2 to 5;

FIG. 8 is a diagrammatic and perspective view of an example of a pre-tensioning instrument of the disclosure;

DETAILED DESCRIPTION OF EMBODIMENTS

Figure 1:
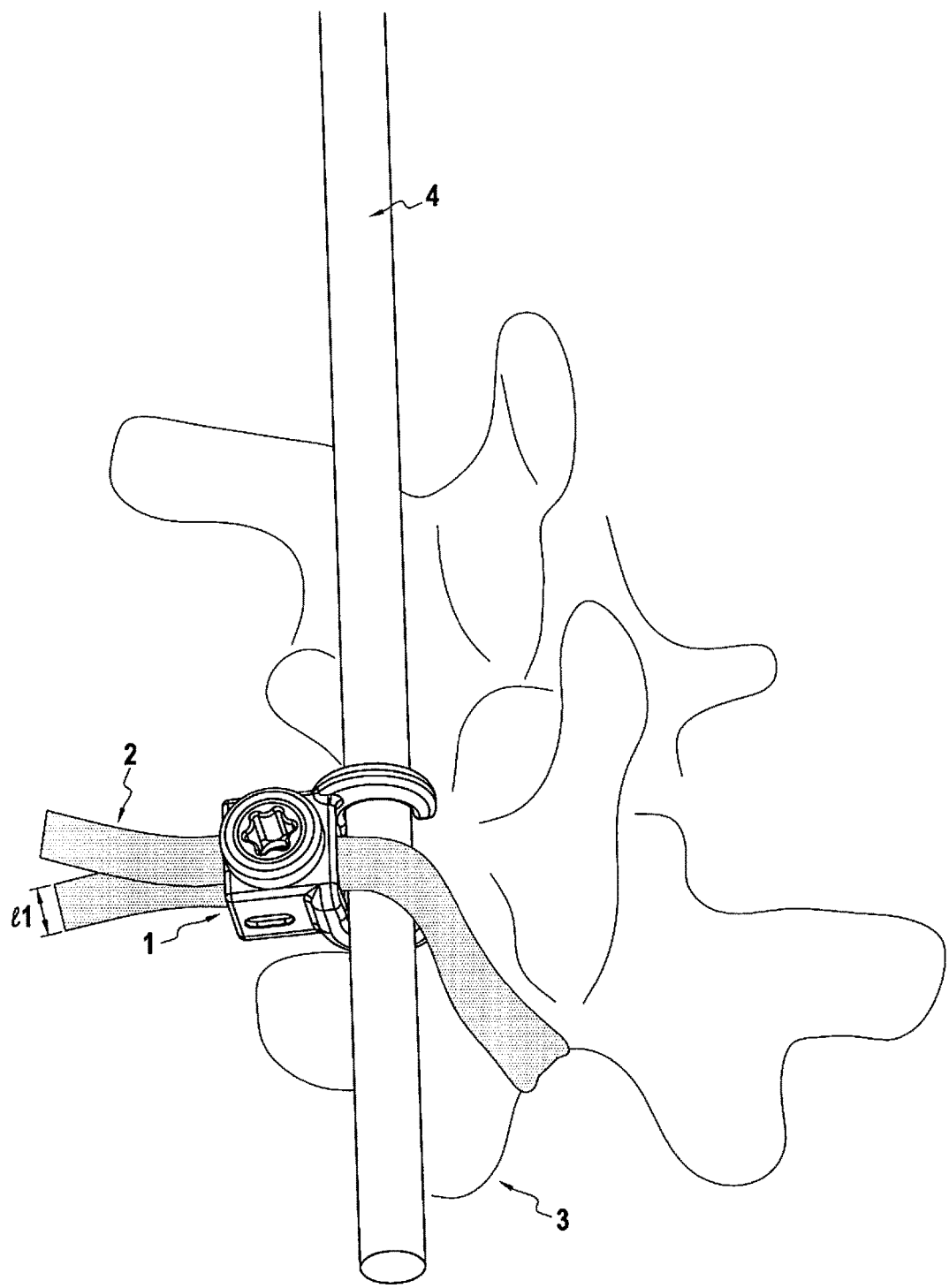
FIG. 1 is a diagrammatic perspective view of an implantable connector fastening an elongate element arranged around a portion of a vertebral body and a longitudinal bar.

FIG. 1 shows an implantable connector 1 (also referred to in the present text as an implant) fastening an elongate element 2 of width 11, in particular a flat element, that is arranged around a portion of a vertebral body 3 and around a longitudinal bar 4. Prior to being fastened in its state wrapped around the portion of the vertebral body 3, said elongate element 2 is tensioned using a tensioning ancillary instrument of the disclosure, possibly in combination with a pre-tensioning ancillary instrument of the disclosure.

FIGS. 2 to 5 show a first example of a tensioning instrument 5 of the disclosure comprising a body 6 having proximal and distal ends 6a and 6b and extending along a longitudinal axis L. The tensioning instrument 5 also comprises a carriage 7 that is movable along the longitudinal axis L, and a fastener device 8 for fastening to the elongate element 2. The instrument 5 also has a rotary shaft 9 that is rotatable about the longitudinal axis L of the body 6, the shaft 9 being configured to co-operate with the carriage 7 in such a manner that rotation of the shaft 9 drives movement in translation of the carriage 7 along the longitudinal axis L and correspondingly moves the carriage 7 away from the distal end 6b of the body 6. The shaft 9 has a portion 10 extending beyond the proximal end 6a of the body 6 and configured to be coupled with a torque actuator device, such as the device 11 shown in FIG. 9. The fastener device 8 comprises a jaw-forming assembly 12 extending in two planes p1 and p2 that slope mutually and that slope relative to the longitudinal axis L of the body. The jaws 12 are configured to be movable and actuatable by a grip member 13 in order to place the elongate element 2 between said jaws 12. In this specific example, the jaw-forming assembly 12 has a locking member 13a serving to block said jaws 12 in the open position. The locking member 13a thus comprises two facing lugs arranged in the grip member 13 and suitable for coming into abutment against the carriage 7 in order to lock the jaw-forming assembly 12 in the open position.

The tensioning instrument 5 has a rapid unlocking device 14 for decoupling the carriage 7 from the rotary shaft 9. The instrument 5 has a clutching and declutching device 15 enabling the carriage 7 to be passed from a declutched position in which the carriage 7 is free to slide longitudinally relative to the longitudinal axis of the rotary shaft 9 to a clutched position in which the carriage 7 is coupled to the rotary shaft 9, or vice versa by using the rapid unlocking device 14. The clutching and declutching device 15 has a support 16 housing a cam 17 in connection with an anvil 18 projecting from a fork 19 having a partially annular bottom contact surface 19a with a thread corresponding to the thread of the rotary shaft 9. The device 15 also has a part 20 in the form of a hollow tube with a window 21 suitable for receiving the fork 19 moving in translation along the axis A. Said part 20 thus has a housing 22 suitable for receiving a portion of the rotary shaft 9. The device 15 also has two return members 23, in particular springs in the form of spring blades that are arranged between the bottom face of the anvil 18 and the top face of the fork 19. The device 15 also has an actuator member 24 acting as the rapid unlocking device 14, such as a lever mounted to pivot about an axis T extending transversely to the longitudinal axis L of the cylinder 6. The various parts of the device 15 are secured to one another, in particular by fastener elements 27. The actuator member 24 is thus configured so that when actuated it decouples the carriage 7 from the rotary shaft 9.

Furthermore, the body 6 has a spring 28 mounted on the rotary shaft 9 and extending longitudinally between the proximal end 6a of the body 6 and the carriage 7. The carriage 7 has a longitudinal slot 30 for receiving the elongate element, in particular two superposed portions of said elongate element. The jaws 12 may have teeth. The slot 30 is arranged above the jaw-forming assembly 12.

The proximal end 6b of the body 6 has a coupling member 31 suitable for being coupled with a removable handle 32 and configured so as to allow the handle 32 to pivot around the longitudinal axis L of the body 6. The removable handle 32 includes a ring having at least one tooth 33a on its periphery suitable for co-operating with a notch in a notched ring 34 mounted on the proximal end 6a of the body 6. The coupling member 31 may have a clamping ring 35 for clamping the ring 33 having at least one tooth 33a together with the notched ring 34 so as to block the coupling between said rings 33 and 34. In particular, the proximal end 6a of the body 6 has a threaded portion on which it is possible to screw the clamping ring 35.

Figure 9:
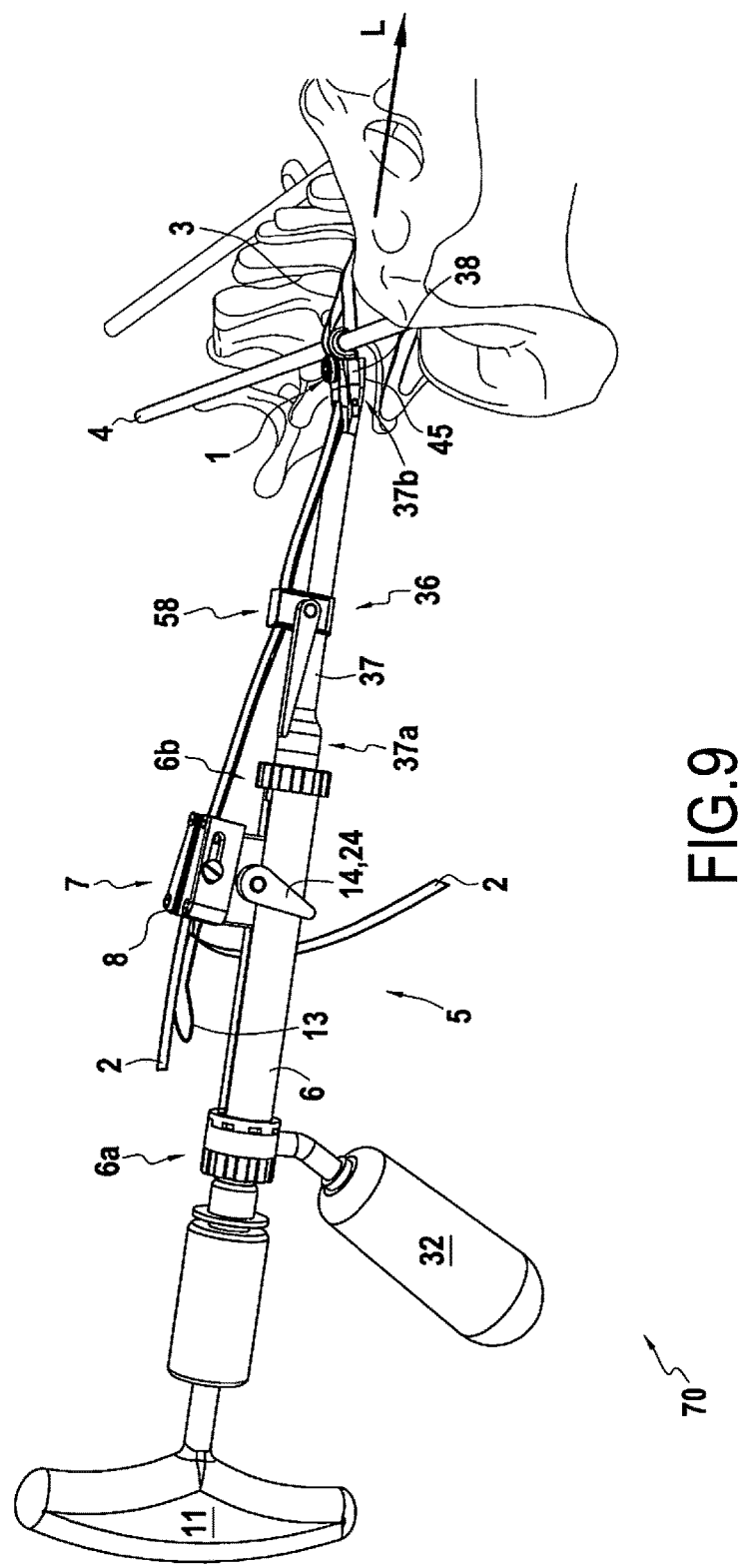
FIG. 9 is a diagrammatic perspective view of an assembly of the present disclosure while in operation, the assembly comprising the tensioning instrument shown in FIGS. 2 to 5 and the pre-tensioning instrument shown in FIG. 8.

FIG. 8 shows a pre-tensioning instrument 36 used in an assembly 70 of the disclosure that also comprises the tensioning instrument 5, and that is shown in operation in FIG. 9. The pre-tensioning instrument 36, as shown in FIG. 8, comprises a rod 37 having proximal and distal ends 37a and 37b, the distal end 37b being provided with a bearing device 38 for bearing against an implant, and in this specific example against an implantable connector, such as the connector 1 shown in FIG. 1. The rod 37 extends along the longitudinal axis L and has a guide and blocking device 58 for guiding and blocking an elongate element such as the elongate element 2 along the longitudinal axis L. The guide and blocking device 58 has an anti-reverse blocker 39 allowing the elongate element to move longitudinally along the longitudinal axis L in the guide and blocking device 58 towards the proximal end 37a of the rod 37, while preventing longitudinal movement of the elongate element along the longitudinal axis L towards the distal end 37b of the rod 37. In this specific example, the rod 37 is configured to be received in a housing 40 arranged in the guide and blocking device 58 to secure the rod 37 to the guide and blocking device 58. The anti-reverse blocker 39 comprises an unlocking member 41 that, when actuated, allows the elongate element to move longitudinally towards the distal end 37b of the rod 37. The anti-reverse blocker 39 has a longitudinal passage 42 with a top bearing surface 42a constituting a guide portion for guiding the longitudinal movement of the elongate element. The guide and blocking device 58 also has a blocking element 43 configured to block the elongate element against the top bearing surface 42a while preventing longitudinal movement of the elongate element towards the distal end 37b of the rod 37. The blocking element 43 is mounted to pivot about an axis T extending transversely relative to the longitudinal direction L of the rod 37. The unlocking member 41 comprises a lever 44 configured to actuate the blocking element 43. The guide and blocking device 58 is configured to have two superposed portions of the elongate element pass therethrough, each of said portions extending a respective first or second free end of the elongate element. In this specific example, the blocking element 43 is a cam mounted on a return member, in particular a cylindrical spring.

The distal end 37b of the rod 37 has a head 45 that includes the bearing device 38, the head 45 is provided with a housing 46 configured to receive at least a portion of the implant, and in particular at least part of the connector 1. The housing 46 includes an opening 47 for passing and guiding the elongate element. The opening 47 has a bottom wall 48 sloping relative to the longitudinal axis L of the rod 37 to guide the elongate element towards the guide and blocking device 58. The opening 47 forms a duct 49 leading to a window 50, said duct 49 having an inlet orifice 49a and an outlet orifice 49b for the elongate elements that are spaced apart by a determined distance d. The duct 49 has top and bottom walls, the bottom wall being the sloping bottom wall 48. The opening 47 has a coupling member 51 for coupling with the implant, in particular the connector 1, in order to secure the head 45 in releasable manner to the implant, the connector 1 in this example. The proximal end 37a of the rod 37 is provided with a coupling member 52 for coupling with the distal end 6b of the body 6 of the tensioning instrument 5.

In FIG. 9, the tensioning instrument 5 is shown in operation coupled with the pre-tensioning instrument 36 for simplification purposes. Nevertheless, on reading the present description, the person skilled in the art can readily understand that the tensioning instrument 5 can tension the elongate element independently of the pre-tensioning instrument 36, providing the tensioning instrument 5 has a bearing device for bearing against the implant and arranged in particular at the distal end 6b of the body 6. For example, the bearing device 38 including the head 45 of the pre-tensioning instrument 36 could be arranged at or extending the distal end 6b of the body 6. In the assembly 70 shown in operation in FIG. 9, the pre-tensioning instrument 36 acts as a bearing device for the tensioning instrument 5. When tensioning the elongate element 2, the first and second free ends of the elongate element leaving the connector 1 and the head 45, and in particular the outlet orifice 49b of the duct 49, are passed together through the guide and blocking device 58 and then the fastener device 8 of the carriage 7. The surgeon can then exert first manual traction for tensioning the superposed portions of the elongate element arranged in the devices 8 and 58, while opening the jaw-forming assembly 12 using the grip member 13. The surgeon can also adjust the position of the handle 32 by causing it to pivot about the longitudinal axis L of the body 6 in order to have better access to the implantation zone. The surgeon then couples the torque device 11 with the projecting portion 10 of the shaft 9 and can actuate the device 11, thereby causing the carriage 7 to move towards the distal end 6a of the body 6 and correspondingly tensioning the elongate element 2. The elongate element 2 can also be seen to move longitudinally in the guide and blocking device 58. The elongate element 2 may move along the longitudinal axes of the body 6 and of the rod 37, which axes are parallel, and in particular coincide. The torque device 11 may be an automatic release device that ensures that it is not possible to exceed a predetermined tightening force. Where necessary, it is possible to relax the tension immediately by means of the rapid unlocking device 14 including the lever 24, thus enabling the carriage 7 to be declutched from the rotary shaft 9. It is possible to reclutch the carriage 7 to the rotary shaft 9 by actuating the unlocking device 14. The tension applied to the elongate element 2 is released automatically, and in accelerated manner because of the spring 28. Even when the tension applied to the elongate element is released at the carriage 7, the elongate element 2 may remain under tension by means of the guide and blocking device 58 including an anti-reverse blocker. Where necessary, it is also possible to release the tension at the guide and blocking device 58 by using the unlocking member 41 having the lever 44.

The window 39 makes it possible to shift the outlet of the elongate element 2 from the connector 1 through a distance of approximately d. This provision enables the application of tension to be shifted onto the window 50 so as to avoid applying it directly on the connector 1, thereby limiting any risk of decoupling the connector 1 from the head 45.

Furthermore, the slopes of the planes p1 and p2 of the jaw-forming assembly 12 relative to the longitudinal axis L of the body 6 prevent the elongate element 2, when put under tension, from disengaging the blocking element 43 from the top bearing surface 42a.

In this specific example, the bearing device 38 bears against the connector 1 and not against the longitudinal bar 4.

When elongate element is correctly tensioned and when the vertebral level has been corrected, the surgeon actuates the device for fastening the elongate element to the implant, in this example the connector 1. The surgeon can also decouple the tensioning instrument 5 from the instrument 36 and adjust the tension on the other elongate elements without actuating the device fastening the elongate element to the connector, so as to be able to correct a plurality of vertebral levels, should that be necessary.

Figure 2:
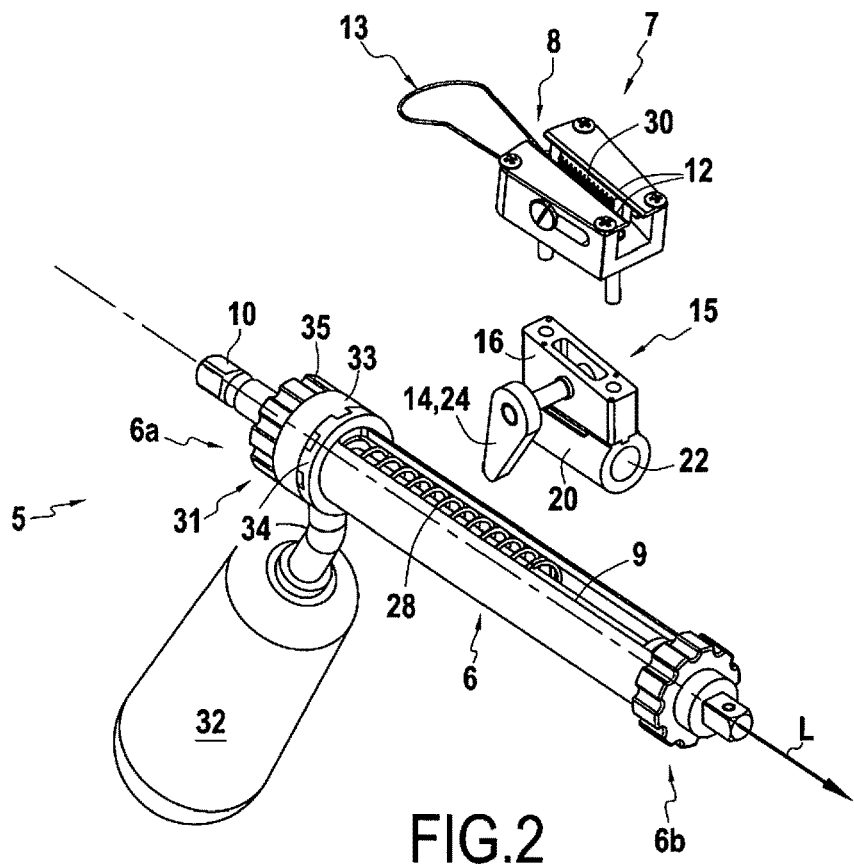
FIG. 2 is a partially exploded diagrammatic perspective view of a first variant of a tensioning instrument of the disclosure.
Figure 3:
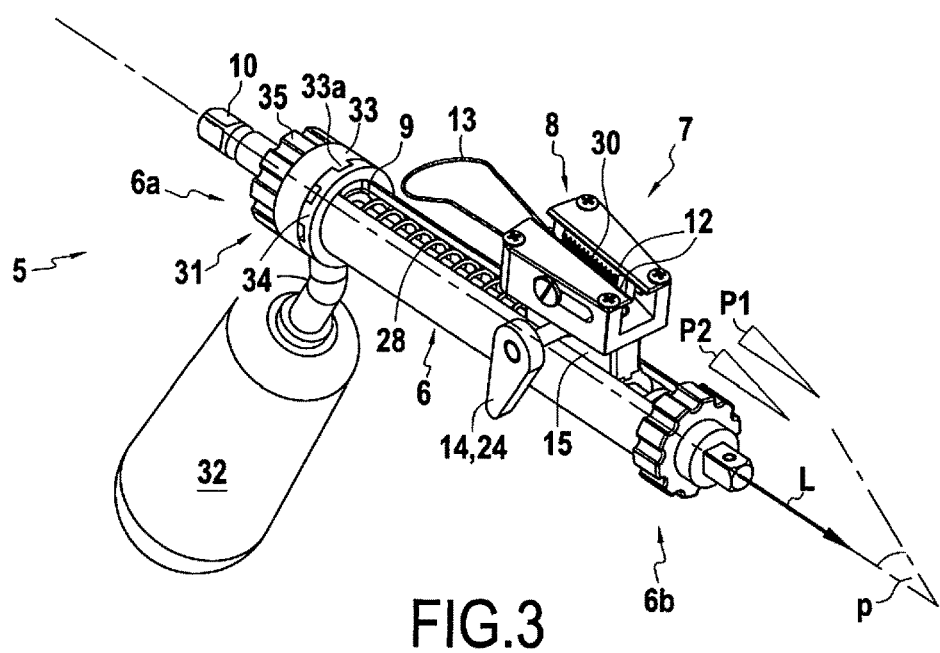
FIG. 3 is a diagrammatic perspective view of the tensioning instrument shown in FIG. 2.
Figure 4:
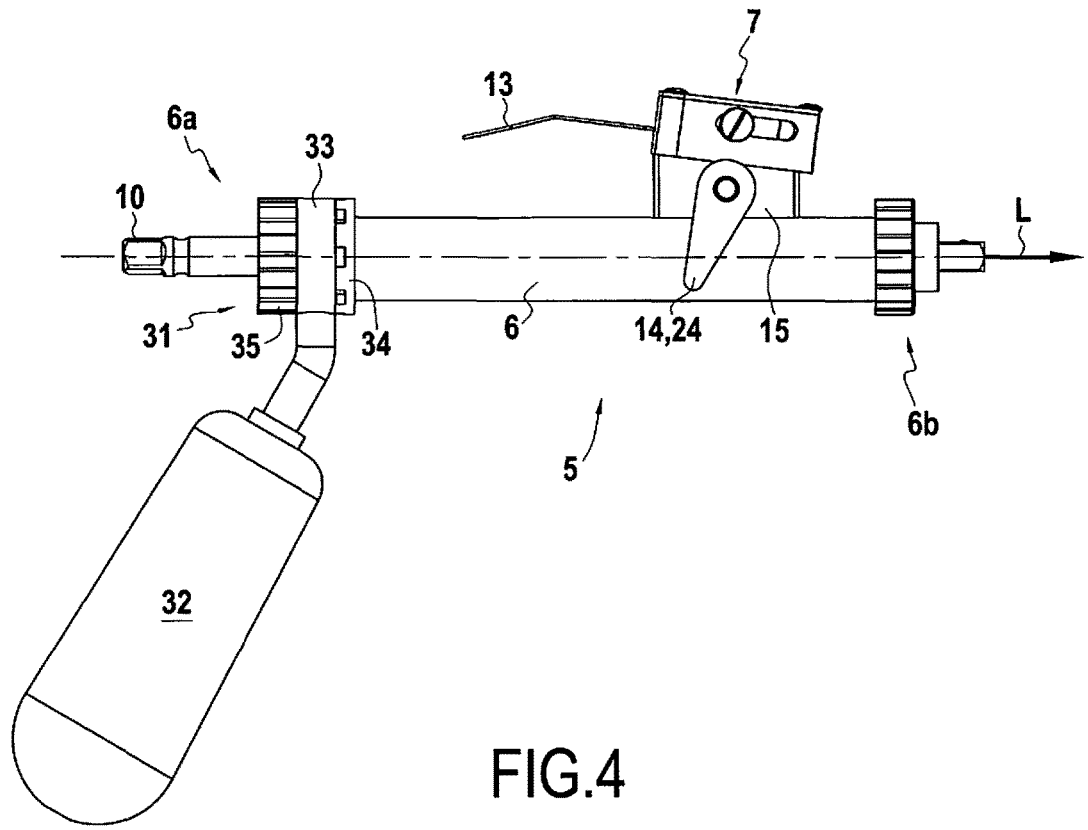
FIG. 4 is a side view of the instrument shown in FIGS. 2 and 3.
Figure 5:
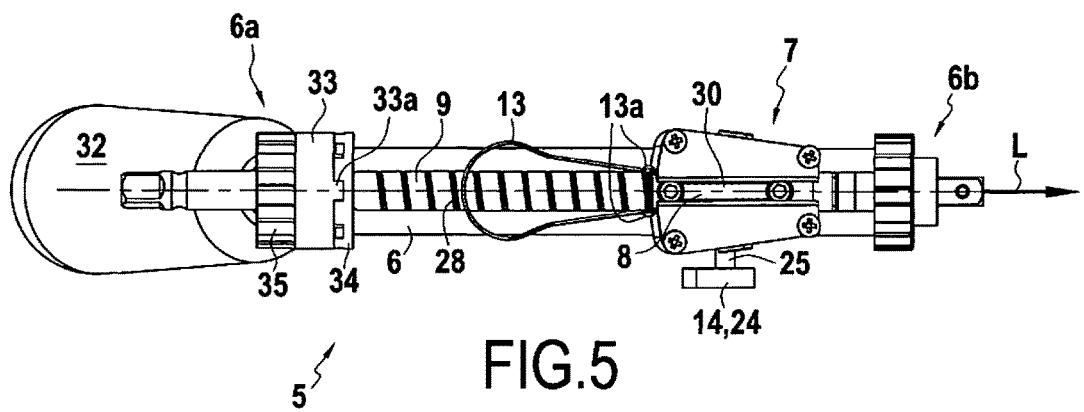
FIG. 5 is a plan view of the instrument shown in FIGS. 2, 3, and 4.
Figure 10:
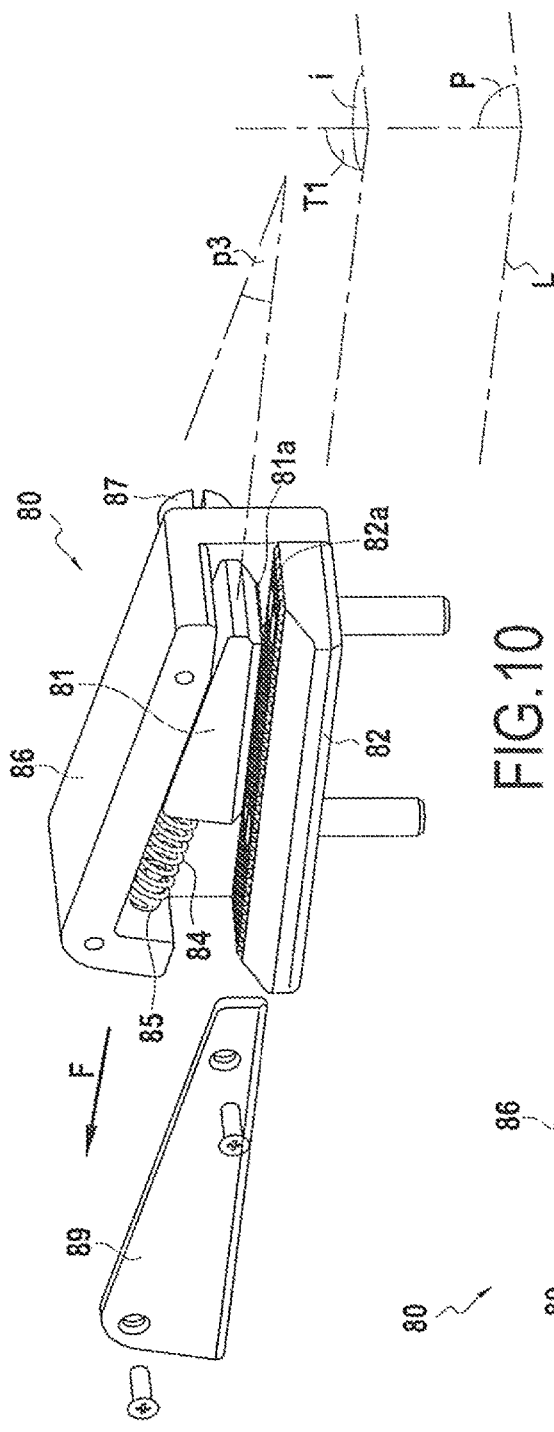
FIG. 10 is a diagram showing a variant of the jaw-forming assembly of the fastener device shown in FIGS. 2 and 3.

FIG. 10 shows a variant of the jaw-forming assembly 12 of the fastener 8 as shown in FIGS. 2 and 3. The jaw-forming assembly 80 shown in FIG. 10 is turned through 90° relative to the jaw-forming assembly 12 of FIG. 2.

Figure 11:
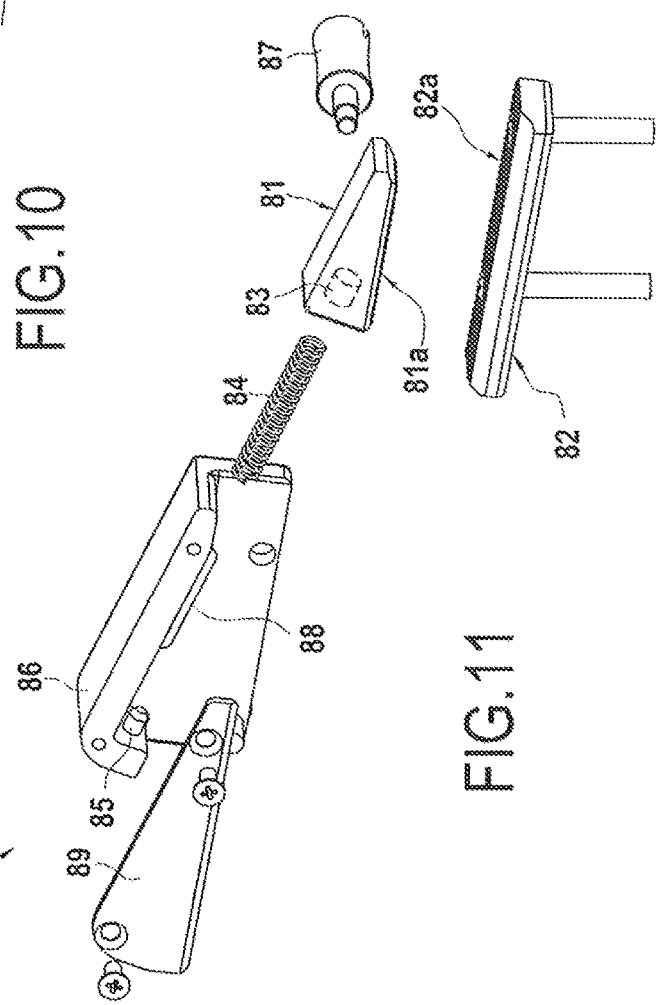
FIG. 11 is an exploded view of the jaw-forming assembly shown in FIG. 10.

As shown also in FIG. 11, this jaw-forming assembly 80 has a top jaw 81 and a bottom jaw 82, the top jaw 81 extending in a plane p3 that slopes relative to the bottom jaw 82 and/or relative to the longitudinal axis L of the cylindrical body 6. The bottom jaw 82 is in a plane i parallel to the longitudinal plane P of the cylindrical body 6. The top jaw 81 moves away from the bottom jaw 82 (which remains stationary since it is secured to the clutching and declutching device), in order to receive at least a portion of the elongate element in a transverse plane T1, in particular substantially transversely relative to the longitudinal plane P of the cylindrical body 6.

More particularly, the top jaw 81 has a first housing 83 receiving a first end of the spring 84, the second end of the spring 84 co-operating with a projection 85 projecting from the main part 86 forming a portion of the jaw-forming assembly 80. The top jaw 81 has a second housing (not visible in the figures) configured to receive a portion of the coupling member 87. The main part 86 also has a slot 88 in which the coupling member 87 in connection with the second housing of the top jaw 81 can move in translation.

The jaw-forming assembly 80 also has a cover 89 for fastening on the main part 86, thereby reducing the size of the side opening for passing the elongate element.

In operation, the top jaw 81 is moved away from the bottom jaw 82 by exerting traction along arrow F on a grip member (not shown), such as the grip member 13 shown in FIGS. 2 and 3, in connection with the projection 85 so as to place the elongate element 2 between the two jaws 81 and 82. When the traction exerted for compressing the spring 84 is released, the top jaw 81 returns to its rest position and blocks the elongate element 2 by pinching against the bottom jaw 82.

In this specific example, each of the top and bottom jaws 81 and 82 has a respective face with a contact portion 81a, 82a coming into contact with at least a portion of the elongate element 2. Said contact portions 81a and 82a are knurled, in particular they have knurling of pyramid shape. The pyramid-shaped knurling of a given contact portion 81a may be arranged in a staggered configuration relative to the knurling of the opposite contact portion 82a so as to improve the pinching and thus improve the blocking of the elongate element.

The jaw-forming assembly 80 may enable the elongate element 2 (at least two superposed portions thereof) as clamped between said jaws 81 and 82 to be arranged in a plane that is parallel to the longitudinal plane P of the cylindrical body 6, thereby preventing it from twisting.

The invention claimed is:

1. A tensioning ancillary instrument for tensioning an elongate element to fasten an implant on a portion of bone, in particular at least a portion of a vertebral body, by surrounding said portion of bone at least in part, said instrument comprising:
   a body having proximal and distal ends, the distal end being provided with a device for bearing against the implant, said body extending along a longitudinal axis,
   the instrument further comprising a carriage that is movable along the longitudinal axis, and
   a fastener device for fastening to the elongate element,
   wherein the instrument includes a rotary shaft rotatable about the longitudinal axis of the body, the shaft being configured to co-operate with the carriage in such a manner that rotation of the shaft drives movement of the carriage in translation along the longitudinal axis and correspondingly moves the carriage away from the distal end of the body and tensions the elongate element,
   wherein the instrument includes a clutching and declutching device for clutching and declutching the carriage and the rotary shaft, the carriage having a declutched position in which the carriage is free to slide longitudinally relative to the longitudinal axis of the rotary shaft, and a clutched position in which the carriage is coupled with the rotary shaft, and
   wherein the instrument includes a rapid unlocking device for decoupling the carriage from the rotary shaft.

2. The instrument according to claim 1, wherein the rotary shaft includes a portion extending beyond the proximal end of the body and configured to be coupled with a torque actuator device.

3. The instrument according to claim 1, wherein the fastener device comprises a jaws-forming assembly extending in two planes that slope relative to each other and that slope relative to the longitudinal axis of the body.

4. The instrument according to claim 3, wherein the jaws-forming assembly is configured to be movable and actuatable by a grip member in order to place the elongate element between said jaws-forming assembly.

5. The instrument according to claim 1, wherein the rapid unlocking device includes a lever that is configured, when actuated, to decouple the carriage from the rotary shaft.

6. The instrument according to claim 1, wherein the body includes a spring mounted on the rotary shaft and extending longitudinally between a proximal end of the body and the carriage.

7. The instrument according to claim 1, wherein the carriage includes a longitudinal slot for receiving the elongate element.

8. The instrument according to claim 7, wherein the slot is arranged above the fastener device, which comprises a jaws-forming assembly.

9. The instrument according to claim 1, wherein the proximal end of the body includes a coupling member suitable for being coupled with a removable handle and configured so as to allow the removable handle to pivot about the longitudinal axis of the body.

10. The instrument according to claim 1, wherein the carriage includes a longitudinal slot for receiving two superposed portions of said elongate element.

11. An assembly comprising a tensioning instrument according to claim 1, wherein the assembly includes a pre-tensioning ancillary instrument including:
   a bearing device, wherein said device for bearing against the implant is the bearing device of said pre-tensioning instrument, and
   a rod having proximal and distal ends, wherein the rod includes a guide and a blocking device for guiding and blocking the elongate element along the longitudinal axis, and said guide and blocking device includes an anti-reverse blocker allowing the elongate element to move in said guide and blocking device longitudinally towards the proximal end of the rod, and preventing the elongate element moving longitudinally towards the distal end of the rod.

12. The assembly according to claim 11, wherein the distal end is provided with the bearing device for bearing against said implant, said rod extending along a longitudinal axis.

13. The assembly according to claim 11, wherein the anti-reverse blocker includes an unlocking member that, when actuated, allows the elongate element to move longitudinally towards the distal end of the rod.

14. The assembly according to claim 13, wherein the unlocking member includes a lever configured to actuate a blocking element.

15. The assembly according to claim 11, wherein the anti-reverse blocker has a longitudinal passage with a top bearing surface constituting a guide portion for guiding the longitudinal movement of the elongate element.

16. The assembly according to claim 15, wherein the guiding and blocking device further comprises a blocking element configured to block the elongate element against the top bearing surface, while preventing the elongate element from moving longitudinally towards the distal end of the rod.

17. The assembly according to claim 16, wherein the blocking element is mounted rotatably about an axis extending transversely to the longitudinal direction of the rod.

18. The assembly according to claim 11, wherein the distal end of the rod has a head that includes the bearing device, the head is provided with a housing configured to receive at least a portion of the implant, the housing having an opening for passing and guiding the elongate element.

19. An assembly comprising:
   a tensioning ancillary instrument for tensioning an elongate element to fasten an implant on a portion of bone, in particular at least a portion of a vertebral body, by surrounding said portion of bone at least in part, said tensioning ancillary instrument comprising:
      a body having proximal and distal ends, the distal end being provided with a device for bearing against the implant, said body extending along a longitudinal axis,
      a carriage that is movable along the longitudinal axis, and a fastener device for fastening to the elongate element, wherein the tensioning ancillary instrument includes a rotary shaft rotatable about the longitudinal axis of the body, the shaft being configured to co-operate with the carriage in such a manner that rotation of the shaft drives movement of the carriage in translation along the longitudinal axis and correspondingly moves the carriage away from the distal end of the body and tensions the elongate element, wherein the tensioning ancillary instrument includes a clutching and declutching device for clutching and declutching the carriage and the rotary shaft, the carriage having a declutched position in which the carriage is free to slide longitudinally relative to the longitudinal axis of the rotary shaft, and a clutched position in which the carriage is coupled with the rotary shaft, and wherein the assembly further comprises a pre-tensioning ancillary instrument including:

a bearing device, wherein said device for bearing against the implant is the bearing device of said pre-tensioning ancillary instrument, and a rod having proximal and distal ends, wherein the rod includes a guide and a blocking device for guiding and blocking the elongate element along the longitudinal axis, and said guide and blocking device includes an anti-reverse blocker allowing the elongate element to move in said guide and blocking device longitudinally towards the proximal end of the rod, and preventing the elongate element moving longitudinally towards the distal end of the rod.

20. The assembly according to claim 19, wherein the anti-reverse blocker includes an unlocking member that, when actuated, allows the elongate element to move longitudinally towards the distal end of the rod.

21. The assembly according to claim 19, wherein the anti-reverse blocker has a longitudinal passage with a top bearing surface constituting a guide portion for guiding the longitudinal movement of the elongate element.

* * * * *